(12) United States Patent
Ogawa et al.

(10) Patent No.: US 9,632,573 B2
(45) Date of Patent: Apr. 25, 2017

(54) MEDICAL MANIPULATOR AND METHOD OF CONTROLLING THE SAME

(75) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1014 days.

(21) Appl. No.: 13/566,012

(22) Filed: Aug. 3, 2012

(65) Prior Publication Data

US 2013/0035697 A1 Feb. 7, 2013

Related U.S. Application Data

(60) Provisional application No. 61/515,203, filed on Aug. 4, 2011.

(51) Int. Cl.
*G06F 3/01* (2006.01)
*A61B 17/29* (2006.01)
(Continued)

(52) U.S. Cl.
CPC .............. *G06F 3/01* (2013.01); *A61B 17/29* (2013.01); *A61B 17/32002* (2013.01); *A61B 18/1402* (2013.01); *A61B 34/30* (2016.02); *A61B 34/37* (2016.02); *A61B 34/74* (2016.02); *A61B 34/76* (2016.02); *A61B 34/77* (2016.02); *A61B 46/10* (2016.02); *A61B 90/50* (2016.02);
(Continued)

(58) Field of Classification Search
CPC . A61B 19/201; A61B 19/5244; A61B 19/203; A61B 19/20; A61B 19/52
USPC .................. 606/130, 205, 170, 174
See application file for complete search history.

(56) References Cited

U.S. PATENT DOCUMENTS

| 3,139,990 A | 7/1964 | Jelatis et al. |
| 3,923,166 A | 12/1975 | Fletcher et al. |

(Continued)

FOREIGN PATENT DOCUMENTS

| CN | 101027010 A | 8/2007 |
| CN | 101167658 A | 4/2008 |

(Continued)

OTHER PUBLICATIONS

Notice of Allowance dated Jan. 20, 2015 from related U.S. Appl. No. 13/566,023.

(Continued)

*Primary Examiner* — Shawki S Ismail
*Assistant Examiner* — Muhammad S Islam
(74) *Attorney, Agent, or Firm* — Scully, Scott, Murphy & Presser, P.C.

(57) ABSTRACT

In a medical manipulator configured to have a manipulation unit including a first input unit and a second input unit that are exchangeable, a signal generation unit configured to process an input with respect to the manipulation unit based on a predetermined process condition and to generate a manipulation signal, an operating unit configured to be operated by the manipulation signal, and a detection unit configured to recognize a type of a used input unit, the process condition corresponded to the first input unit and the process condition corresponded to the second input unit differ, and the signal generation unit generates the manipulation signal based on the process condition corresponded to the input unit recognized by the detection unit.

20 Claims, 12 Drawing Sheets

(51) Int. Cl.
  *A61B 17/32*   (2006.01)
  *A61B 18/14*   (2006.01)
  *B25J 13/02*   (2006.01)
  *A61B 90/50*   (2016.01)
  *A61B 34/30*   (2016.01)
  *A61B 46/10*   (2016.01)
  *A61B 34/37*   (2016.01)
  *A61B 17/068*  (2006.01)
  *A61B 17/00*   (2006.01)
  *A61B 46/23*   (2016.01)
  *A61B 34/20*   (2016.01)
  *A61B 90/00*   (2016.01)
  *A61B 34/00*   (2016.01)
  *A61B 90/90*   (2016.01)

(52) U.S. Cl.
  CPC ........... *B25J 13/02* (2013.01); *A61B 17/068* (2013.01); *A61B 34/20* (2016.02); *A61B 34/25* (2016.02); *A61B 46/23* (2016.02); *A61B 90/90* (2016.02); *A61B 2017/00119* (2013.01); *A61B 2017/00477* (2013.01); *A61B 2017/00482* (2013.01); *A61B 2034/2055* (2016.02); *A61B 2034/2065* (2016.02); *A61B 2090/065* (2016.02); *A61B 2090/067* (2016.02); *A61B 2090/0803* (2016.02); *A61B 2090/0813* (2016.02); *A61B 2090/0814* (2016.02); *A61B 2090/364* (2016.02); *A61B 2090/3937* (2016.02); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | |
|---|---|---|---|
| 4,672,281 A | 6/1987 | Yagusic et al. | |
| 4,830,569 A | 5/1989 | Jannborg | |
| 4,872,803 A | 10/1989 | Asakawa | |
| 5,214,969 A | 6/1993 | Adkins et al. | |
| 5,603,723 A | 2/1997 | Aranyi et al. | |
| 5,632,432 A | 5/1997 | Schulze et al. | |
| 5,649,956 A | 7/1997 | Jensen et al. | |
| 5,656,903 A | 8/1997 | Shui et al. | |
| 5,712,543 A | 1/1998 | Sjostrom | |
| 5,760,530 A | 6/1998 | Kolesar | |
| 5,762,458 A | 6/1998 | Wang et al. | |
| 5,784,542 A | 7/1998 | Ohm et al. | |
| 5,817,119 A * | 10/1998 | Klieman | A61B 17/29 606/170 |
| 5,836,869 A | 11/1998 | Kudo et al. | |
| 5,855,583 A | 1/1999 | Wang et al. | |
| 5,871,493 A | 2/1999 | Sjostrom et al. | |
| 5,876,325 A * | 3/1999 | Mizuno | A61B 1/00048 600/102 |
| 6,007,550 A | 12/1999 | Wang et al. | |
| 6,039,748 A | 3/2000 | Savage et al. | |
| 6,063,095 A | 5/2000 | Wang et al. | |
| 6,082,797 A | 7/2000 | Antonette | |
| 6,090,122 A | 7/2000 | Sjostrom et al. | |
| 6,102,850 A | 8/2000 | Wang et al. | |
| 6,132,368 A | 10/2000 | Cooper | |
| 6,132,441 A | 10/2000 | Grace | |
| 6,206,903 B1 | 3/2001 | Ramans | |
| 6,246,200 B1 | 6/2001 | Blumenkranz et al. | |
| 6,328,752 B1 | 12/2001 | Sjostrom et al. | |
| 6,346,072 B1 | 2/2002 | Cooper | |
| 6,430,473 B1 | 8/2002 | Lee et al. | |
| 6,436,107 B1 | 8/2002 | Wang et al. | |
| 6,441,577 B2 | 8/2002 | Blumenkranz et al. | |
| 6,557,558 B1 | 5/2003 | Tajima et al. | |
| 6,574,355 B2 | 6/2003 | Green | |
| 6,587,750 B2 | 7/2003 | Gerbi et al. | |
| 6,602,185 B1 | 8/2003 | Uchikubo | |
| 6,645,196 B1 | 11/2003 | Nixon et al. | |
| 6,666,876 B2 | 12/2003 | Kawai et al. | |
| 6,676,684 B1 | 1/2004 | Morley et al. | |
| 6,685,698 B2 | 2/2004 | Morley et al. | |
| 6,699,177 B1 | 3/2004 | Wang et al. | |
| 6,746,443 B1 | 6/2004 | Morley et al. | |
| 6,783,524 B2 | 8/2004 | Anderson et al. | |
| 6,786,896 B1 | 9/2004 | Madhani et al. | |
| 6,853,879 B2 | 2/2005 | Sunaoshi | |
| 6,866,671 B2 | 3/2005 | Tierney et al. | |
| 6,905,460 B2 | 6/2005 | Wang et al. | |
| 6,913,613 B2 | 7/2005 | Schwarz et al. | |
| 7,083,571 B2 | 8/2006 | Wang et al. | |
| 7,101,363 B2 | 9/2006 | Nishizawa et al. | |
| 7,107,124 B2 | 9/2006 | Green | |
| 7,118,582 B1 | 10/2006 | Wang et al. | |
| 7,273,488 B2 | 9/2007 | Nakamura et al. | |
| 7,295,893 B2 | 11/2007 | Sunaoshi | |
| 7,313,464 B1 | 12/2007 | Perreault et al. | |
| 7,331,967 B2 | 2/2008 | Lee et al. | |
| 7,357,774 B2 | 4/2008 | Cooper | |
| 7,373,219 B2 * | 5/2008 | Nowlin | B25J 9/1689 318/568.11 |
| 7,422,592 B2 | 9/2008 | Morley et al. | |
| 7,476,237 B2 | 1/2009 | Taniguchi et al. | |
| 7,549,998 B2 | 6/2009 | Braun | |
| 7,594,912 B2 | 9/2009 | Cooper et al. | |
| 7,608,083 B2 * | 10/2009 | Lee | A61B 17/0469 606/1 |
| 7,654,431 B2 | 2/2010 | Hueil et al. | |
| 7,666,191 B2 | 2/2010 | Orban, III et al. | |
| 7,674,255 B2 | 3/2010 | Braun | |
| 7,695,481 B2 | 4/2010 | Wang et al. | |
| 7,699,835 B2 | 4/2010 | Lee et al. | |
| 7,699,855 B2 | 4/2010 | Anderson et al. | |
| 7,778,733 B2 | 8/2010 | Nowlin et al. | |
| 7,819,884 B2 | 10/2010 | Lee et al. | |
| 7,819,885 B2 | 10/2010 | Cooper | |
| 7,862,579 B2 | 1/2011 | Ortiz et al. | |
| 7,865,266 B2 | 1/2011 | Moll et al. | |
| 7,955,321 B2 | 6/2011 | Kishi et al. | |
| 8,105,320 B2 | 1/2012 | Manzo | |
| 8,155,479 B2 | 4/2012 | Hoffman et al. | |
| 8,267,958 B2 | 9/2012 | Braun | |
| 8,350,806 B2 | 1/2013 | Nagasaka et al. | |
| 8,423,186 B2 | 4/2013 | Itkowitz et al. | |
| 8,460,277 B2 | 6/2013 | Suarez et al. | |
| 8,496,647 B2 | 7/2013 | Blumenkranz et al. | |
| 8,540,748 B2 | 9/2013 | Murphy et al. | |
| 8,744,137 B2 | 6/2014 | Sakai et al. | |
| 8,845,681 B2 | 9/2014 | Grace | |
| 8,876,858 B2 | 11/2014 | Braun | |
| 8,888,789 B2 | 11/2014 | Prisco et al. | |
| 8,903,549 B2 | 12/2014 | Itkowitz et al. | |
| 8,906,002 B2 | 12/2014 | Kishi et al. | |
| 9,039,681 B2 * | 5/2015 | Wang | G05B 15/02 606/1 |
| 9,283,675 B2 | 3/2016 | Hager et al. | |
| 9,308,009 B2 | 4/2016 | Madan et al. | |
| 9,308,646 B2 | 4/2016 | Lim et al. | |
| 2001/0021859 A1 | 9/2001 | Kawai et al. | |
| 2001/0055062 A1 | 12/2001 | Shioda et al. | |
| 2002/0072736 A1 | 6/2002 | Tierney et al. | |
| 2002/0091374 A1 | 7/2002 | Cooper | |
| 2002/0128552 A1 * | 9/2002 | Nowlin | A61B 34/70 600/427 |
| 2003/0033024 A1 | 2/2003 | Sunaoshi | |
| 2003/0033204 A1 | 2/2003 | Sunaoshi | |
| 2003/0060927 A1 | 3/2003 | Gerbi et al. | |
| 2003/0069471 A1 | 4/2003 | Nakanishi et al. | |
| 2003/0083648 A1 | 5/2003 | Wang et al. | |
| 2003/0100817 A1 | 5/2003 | Wang et al. | |
| 2003/0216723 A1 | 11/2003 | Shinmura et al. | |
| 2004/0092912 A1 | 5/2004 | Jinno et al. | |
| 2004/0111113 A1 | 6/2004 | Nakamura et al. | |
| 2004/0140787 A1 | 7/2004 | Okamoto et al. | |
| 2004/0186345 A1 | 9/2004 | Yang et al. | |

(56) References Cited

U.S. PATENT DOCUMENTS

| | | |
|---|---|---|
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1 | 7/2006 | Daw et al. |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1* | 9/2008 | Kishi .................. B25J 9/1689 700/259 |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1 | 11/2009 | Banju et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1* | 9/2010 | Goldberg ............... A61B 34/30 312/209 |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |
| 2014/0148819 A1* | 5/2014 | Inoue .................... B25J 9/1612 606/130 |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-29810 A | 2/1988 |
| JP | 64-34688 A | 2/1989 |
| JP | 1-271185 A | 10/1989 |
| JP | 2-71980 A | 3/1990 |
| JP | 2-292193 A | 12/1990 |
| JP | 3-161289 A | 7/1991 |
| JP | 5-96477 A | 4/1993 |
| JP | 5-329784 A | 12/1993 |
| JP | 7-1366 A | 1/1995 |
| JP | 7-194609 A | 8/1995 |
| JP | 7-241300 A | 9/1995 |
| JP | 7-246578 A | 9/1995 |
| JP | 7-96182 B2 | 10/1995 |
| JP | 8-66883 A | 3/1996 |
| JP | 8-215204 A | 8/1996 |
| JP | 8-243080 A | 9/1996 |
| JP | 10-128538 A | 5/1998 |
| JP | 11-300662 A | 11/1999 |
| JP | 2000-312684 A | 11/2000 |
| JP | 2001-113481 A | 4/2001 |
| JP | 2001-277157 A | 10/2001 |
| JP | 2001-309920 A | 11/2001 |
| JP | 2002-14287 A | 1/2002 |
| JP | 2002-59380 A | 2/2002 |
| JP | 2002-102248 A | 4/2002 |
| JP | 2002-272758 A | 9/2002 |
| JP | 2002-537884 A | 11/2002 |
| JP | 2003-24336 A | 1/2003 |
| JP | 2003-53685 A | 2/2003 |
| JP | 2003-250812 A | 9/2003 |

(56) References Cited

FOREIGN PATENT DOCUMENTS

| | | |
|---|---|---|
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |
| JP | 2005-312991 A | 11/2005 |
| JP | 2006-61272 A | 3/2006 |
| JP | 2006-167867 A | 6/2006 |
| JP | 2006-288955 A | 10/2006 |
| JP | 2006-321027 A | 11/2006 |
| JP | 2007-29274 A | 2/2007 |
| JP | 2007-38315 A | 2/2007 |
| JP | 2007-98507 A | 4/2007 |
| JP | 2007-105485 A | 4/2007 |
| JP | 3999816 B2 | 10/2007 |
| JP | 2008-282 A | 1/2008 |
| JP | 2008-36793 A | 2/2008 |
| JP | 4058113 B2 | 3/2008 |
| JP | 2008-093270 A | 4/2008 |
| JP | 2008-173724 A | 7/2008 |
| JP | 2008-188109 A | 8/2008 |
| JP | 4129313 B2 | 8/2008 |
| JP | 4176126 B2 | 11/2008 |
| JP | 2009-028157 A | 2/2009 |
| JP | 2009-56164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |
| JP | 2010-76012 A | 4/2010 |
| JP | 2010-524548 A | 7/2010 |
| JP | 2011-509112 A | 3/2011 |
| JP | 2001-087281 A | 4/2011 |
| JP | 2001-277157 A | 10/2011 |
| JP | 2011-206213 A | 10/2011 |
| JP | 2012-000199 A | 1/2012 |
| JP | 2012-12104 A | 1/2012 |
| JP | 2012-91310 A | 5/2012 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | 00/51486 A1 | 9/2000 |
| WO | 00/60421 A2 | 10/2000 |
| WO | 03/049596 A2 | 6/2003 |
| WO | 2006/111966 A2 | 10/2006 |
| WO | WO 2007/047782 A2 | 4/2007 |
| WO | 2007/075864 A1 | 7/2007 |
| WO | WO 2007/111955 A2 | 10/2007 |
| WO | WO 2007/126443 A2 | 11/2007 |
| WO | 2007/138674 A1 | 12/2007 |
| WO | 2008/038184 A2 | 4/2008 |
| WO | 2008/108289 A1 | 9/2008 |
| WO | 2009/034477 A2 | 3/2009 |
| WO | 2009/089614 A1 | 7/2009 |
| WO | 2010/006057 A1 | 1/2010 |
| WO | 2010/093152 A2 | 8/2010 |
| WO | 2010/109932 A1 | 9/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | WO 2012/042949 A1 | 4/2012 |

OTHER PUBLICATIONS

Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Patent Application, namely U.S. Appl. No. 14/169,321.
Extended Supplementary European Search Report dated Mar. 27, 2015 from related European Application No. 12 82 0056.5.
International Search Report dated Oct. 23, 2012 from related International Application No. PCT/JP2012/070414.
International Search Report dated Sep. 4, 2012 from related International Application No. PCT/JP2012/070408.
International Search Report dated Aug. 28, 2012 from related International Application No. PCT/JP2012/069927.
International Search Report dated Sep. 4, 2012 from related International Application No. PCT/JP2012/070415.
International Search Report dated Oct. 16, 2012 from related International Application No. PCT/JP2012/070581.
International Search Report dated Nov. 13, 2012 from related International Application No. PCT/JP2012/070576.
International Search Report dated Sep. 18, 2012 from related International Application No. PCT/JP2012/070417.
International Search Report dated Oct. 30, 2012 from related International Application No. PCT/JP2012/070418.
International Search Report dated Sep. 11, 2012 from related International Application No. PCT/JP2012/070416.
International Search Report dated Sep. 18, 2012 from related International Application No. PCT/JP2012/070407.
International Search Report dated Sep. 18, 2012 from related International Application No. PCT/JP2012/069868.
International Search Report dated Nov. 6, 2012 from related International Application No. PCT/JP2012/069919.
International Search Report dated Sep. 11, 2012 from related International Application No. PCT/JP2012/069696.
U.S. Office Action dated Apr. 9, 2015 received in related U.S. Patent Application, namely U.S. Appl. No. 14/169,675.
U.S. Office Action dated May 8, 2015 received in related U.S. Patent Application, namely U.S. Appl. No. 14/157,920.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.

(56) References Cited

OTHER PUBLICATIONS

English language abstract only of JP 01-234140 published Sep. 19, 1989.
Office Action dated Oct. 19, 2015 received in related U.S. Patent Application, namely U.S. Appl. No. 14/168,525.
Office Action dated Oct. 22, 2015 received in related U.S. Patent Application, namely U.S. Appl. No. 14/151,987.
Office Action dated Nov. 19, 2015 received in related U.S. Patent Application, namely U.S. Appl. No. 14/157,920.
Office Action dated Mar. 24, 2016 received in related U.S. Appl. No. 13/566,047.
Office Action dated Feb. 22, 2016 received in related U.S. Appl. No. 14/168,496.
Japanese Office Action dated Jun. 14, 2016 in related Japanese Patent Application No. 2012-012104.
Office Action dated Jun. 16, 2016 received in related U.S. Appl. No. 14/169,742.
Japanese Office Action dated Jan. 19, 2016 from related Japanese Patent Application No. 2012-036226, together with an English language translation.
Notice of Allowance dated Apr. 22, 2016 issued in U.S. Appl. No. 14/157,920.
European Patent Office Communication dated May 23, 2016 in related European Application No. 12 819 877.7.
Office Action dated May 9, 2016 received in related U.S. Appl. No. 14/170,856.
Japanese Office Action dated Jun. 28, 2016 in related Japanese Patent Application No. 2013-526973.
Japanese Office Action dated Jan. 4, 2017 in related Japanese Patent Application No. 2012-012104.
Office Action dated Feb. 28, 2017 received in related U.S. Appl. No. 14/168,496.

\* cited by examiner

US 9,632,573 B2

MEDICAL MANIPULATOR AND METHOD OF CONTROLLING THE SAME

Priority is claimed on U.S. Provisional Patent Application No. 61/515,203, filed Aug. 4, 2011, the contents of which is incorporated herein by reference.

TECHNICAL FIELD

The present invention relates to a medical manipulator, and more specifically, to a medical manipulator that switches control of an end effector according to an input unit gripped by a surgeon, and a method of controlling the medical manipulator.

BACKGROUND ART

A medical manipulator that manipulates a treatment tool (an end effector) for performing treatment inside a body of a patient, through a manipulation unit, is conventionally known.

Multiple types of end effectors having various shapes such as a needle holder type, a forceps type, a scissors type, a scalpel type, and high-frequency treatment tools according to treatment to be performed are prepared. Usually, the plurality of end effectors are appropriately exchanged or combined and used in each process of surgery.

When the end effector is changed, manipulation details in the manipulation unit are also accordingly changed. Accordingly, it may be difficult to manipulate certain types of end effectors using a single manipulation unit. In order to resolve this problem, providing a plurality of grips (input units) corresponding to multiple types of end effectors and interchangeably mounting the grips on a manipulation unit has been proposed in Japanese Unexamined Patent Application, First Publication No. 2001-087281. This enables a surgeon to manipulate each end effector using a grip most suitable for the end effector.

SUMMARY OF INVENTION

A first aspect of the present invention is a medical manipulator including a manipulation unit configured to have a first input unit and a second input unit that are exchangeable; a signal generation unit configured to process an input with respect to the manipulation unit based on a predetermined process condition and to generate a manipulation signal; an operating unit configured to be operated by the manipulation signal; and a detection unit configured to recognize a type of a used input unit, wherein the process condition corresponded to associated with the first input unit and the process condition corresponded to the second input unit differ, and the signal generation unit generates the manipulation signal based on the process condition corresponded to the input unit recognized by the detection unit.

The process condition may include a setting aspect of a coordinate system in the input unit or may include an origin position of a coordinate system in the input unit.

Further, the process condition may include information for selecting degrees of freedom used for generation of the manipulation signal among degrees of freedom included in the input.

The operating unit may comprise an end effector exhibiting a predetermined function, and at least one of the first input unit and the second input unit may have the same shape as a tool exhibiting the function.

In this case, the process condition may include a scale ratio of an input to the input unit and the manipulation signal or may include information for a filter used at the time of generation of the manipulation signal. Further, the process condition may include an output limit value of the manipulation signal.

The first input unit and the second input unit may comprise a common input mechanism, and the process condition may comprise a type of a function exhibited in the operating unit by an input to the input mechanism.

A second aspect of the present invention is a method of controlling the medical manipulator comprised a manipulation unit configured to include a first input unit and a second input unit that are exchangeable, a signal generation unit configured to process an input with respect to the manipulation unit based on a predetermined process condition and generate a manipulation signal, an operating unit configured to be operated by the manipulation signal, and a detection unit configured to recognize a type of a used input unit, the method including: a step for corresponding different process conditions with the first input unit and the second input unit; a step for recognizing, by the detection unit, a type of a used input unit; and a step for setting, in the signal generation unit, the process condition corresponded to the recognized input unit.

DESCRIPTION OF EMBODIMENTS

A medical manipulator of a first embodiment of the present invention and a method of controlling the same will be described with reference to FIGS. 1 to 10.

Figure 1:
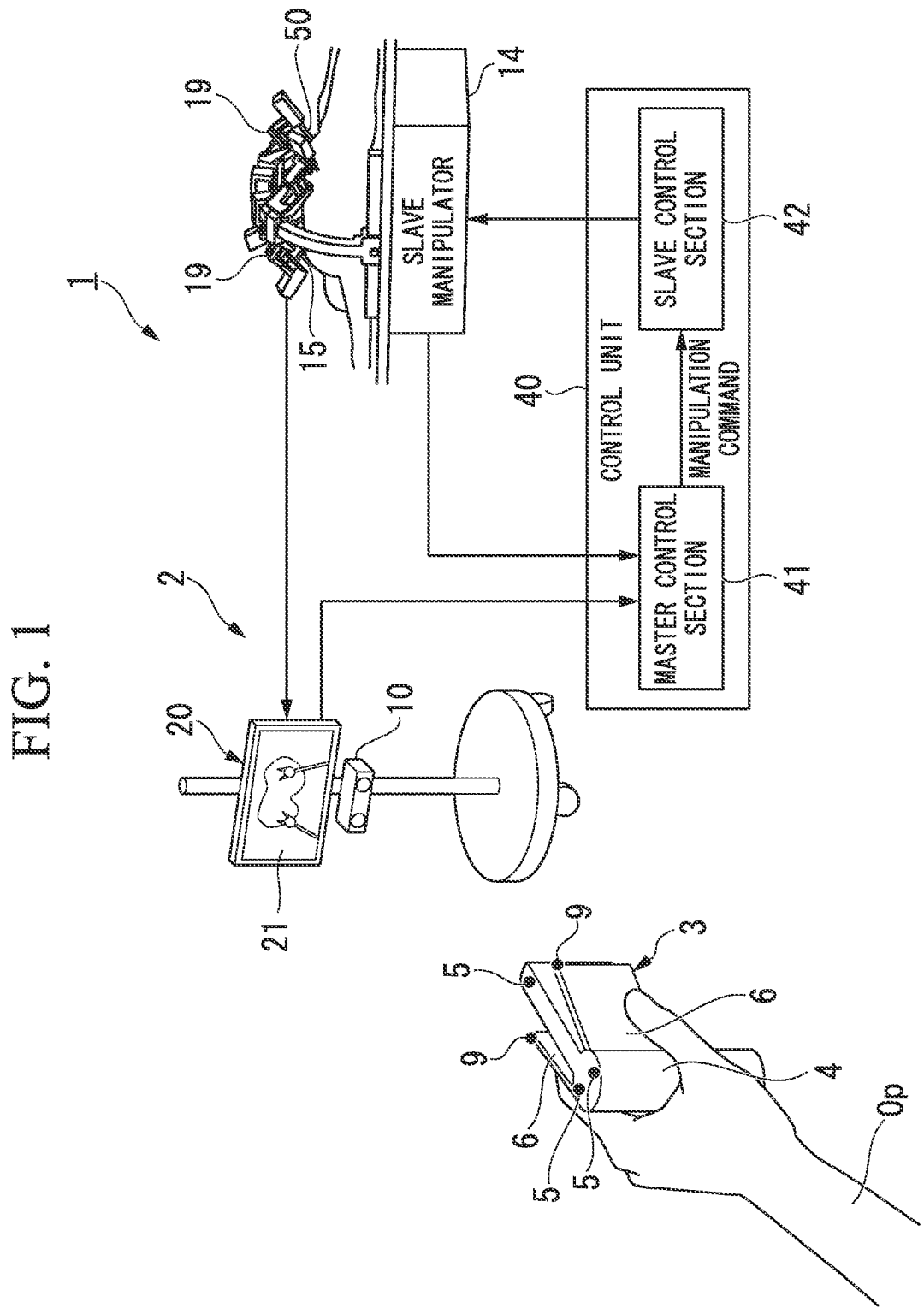
FIG. 1 is a diagram illustrating an overall configuration of a medical manipulator according to a first embodiment of the present invention.

FIG. 1 is a schematic diagram illustrating an overall configuration of a medical manipulator 1 of the present embodiment. As illustrated in FIG. 1, the medical manipulator 1 of the present embodiment includes a master manipulator (a manipulation unit) 2 and a slave manipulator (operating unit) 14. That is, the medical manipulator 1 is a master-slave manipulator for remotely controlling the slave manipulator 14 and a treatment tool (which will be described below) mounted on the slave manipulator 14 so as to follow a manipulation of the master manipulator 2 by a surgeon (a manipulating person) Op.

A manipulation command via the master manipulator 2 is transmitted to a master control unit (a manipulation signal generation unit) 41 of a control unit 40, and a conversion process (which will be described below) is performed based on a predetermined process condition to generate a manipulation signal. The generated manipulation signal is sent to a slave control unit 42. Then, a driving signal based on the manipulation signal is sent from the slave control unit 42 to the slave manipulator 14, and then, the slave manipulator 14 and the treatment tool operate.

The master manipulator 2 includes a first grip (a first input unit) 3 to be held by the surgeon Op, a detection unit 10 that detects the first grip 3, and a display unit 20 that displays an operative field. Further, the medical manipulator 1 includes a plurality of grips to be held by the surgeon Op, which will be described in detail.

Figure 2:
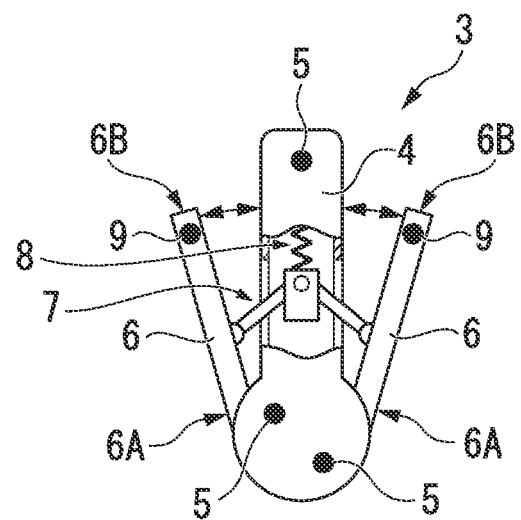
FIG. 2 is a schematic view illustrating a first grip and an end effector of a treatment tool of the medical manipulator according to the first embodiment of the present invention.
Figure 2:
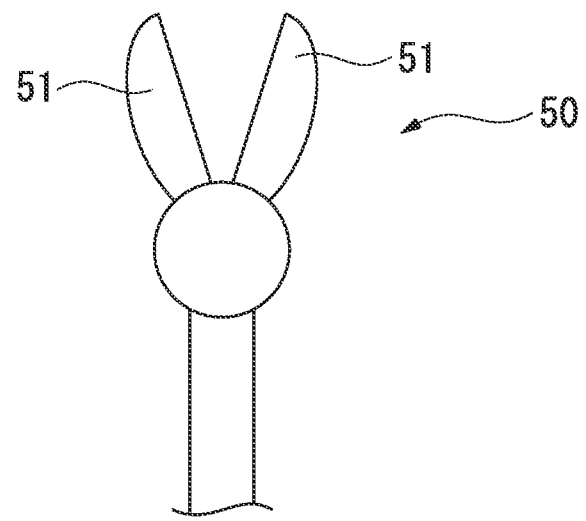

The first grip 3 includes a main body portion 4, and a pair of moving parts 6 movably coupled to the main body portion 4, as illustrated in FIG. 2.

First markers 5 are provided at three separate places on an outer surface of the main body portion 4. The three first markers 5 are arranged so that three sides of a triangle having vertexes that are the first markers 5 have different lengths. As a result, a relative positional relationship among the first markers 5 is specified in the image acquired by the detection unit 10, so that orientation of the main body portion 4 can be calculated.

In one pair of moving parts 6, each first end portion 6A is rotatably supported with respect to the main body portion 4. The moving part 6 is also supported by the main body portion 4 via a link 7 and a biasing member 8, and a second end portion 6B is biased to be separated from the main body portion 4 in a state in which the surgeon Op does not apply force. A second marker 9 is provided in the second end portion 6B of each moving part 6.

A distal end portion of a treatment tool 50 mounted on the slave manipulator 14 is schematically illustrated in a lower portion of FIG. 2. A pair of forceps members 51, which are opened and closed, are provided as an end effector in a distal end of the treatment tool 50. The surgeon Op can perform a manipulation input for closing or opening the forceps members 51 by manipulating the second end portion 6B of the moving part 6 to approach the main body portion 4 or be separated from the main body portion 4.

Figure 3:
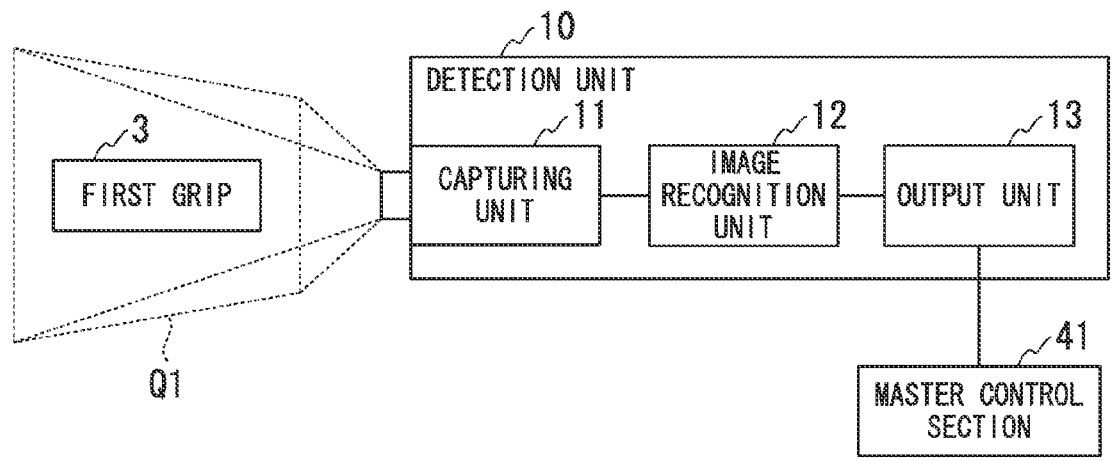
FIG. 3 is a schematic view illustrating a detection unit of the medical manipulator according to the first embodiment of the present invention.

FIG. 3 is a schematic diagram illustrating a configuration of the detection unit 10. The detection unit 10 comprises a capturing unit 11, an image recognition unit 12, and an output unit 13.

The capturing unit 11 comprises a first imaging unit configured to capture from one predetermined direction, and a second imaging unit configured to capture from a different direction from the predetermined direction, and may simultaneously capture two images at different angles with respect to the first grip 3 located within a visual field Q1. The images acquired by the capturing unit 11 are output to the image recognition unit 12.

The image recognition unit 12 discriminates and recognizes the first markers 5 and the second markers 9 from the captured images through a known image recognition process, and acquires coordinates of the first markers 5 and the second markers 9. Further, the image recognition unit 12 discriminates and recognizes a type of a used input unit, for example, by identifying the markers.

The output unit 13 outputs a coordinate of each of the markers 5 and 9 acquired by the image recognition unit 12 as coordinate information to the master control unit 41, and outputs a type of recognized input unit. In the present embodiment, the coordinate information output from the output unit 13 includes information for specifying a position and an orientation of the main body portion 4 of the first grip 3 (first information), and information for specifying a manipulation input state of the moving parts 6 (second information). The coordinate information is output from the output unit 13 according to a predetermined transmission timing irrespective of whether the first grip 3 is moving within the visual field Q1.

Through the above configuration, the surgeon Op can perform a manipulation input for manipulating the end effector of the treatment tool 50 and the slave arm 14 having the treatment tool 50 mounted thereon by holding and manipulating the first grip 3 within a visual field of the capturing unit 11 of the detection unit 10. That is, a position and an orientation of the end effector may be changed by a position and an orientation of the main body portion 4, and an opening and closing state of the forceps members 51 may be changed by a manipulation of the moving parts 6. Further, the position and the orientation of the end effector are controlled based on a predetermined coordinate system set in the main body portion 4.

As illustrated in FIG. 1, the slave manipulator 14 comprises a plurality of slave arms 19 each having an endoscope device 15 and the treatment tool 50 mounted thereon, and an actuator (not shown) that operates the treatment tool 50 and the slave arm 19. Each actuator provided in the slave manipulator 14 operates according to a driving signal output from the slave control unit 42 of the control unit 40. The endoscope device 15 provided in one of the slave arms 19 acquires an image in the operative field including the treatment target or a distal end portion of the treatment tool 50, and outputs the image to the display unit 20.

Further, the endoscope device 15 not be mounted on the slave arm 19 for use and the operative field to be displayed on the display unit 20 may be fixed or may be manually adjusted, for example, by an assistant inside an operating room.

The position and the orientation of the end effector provided in the distal end portion of the treatment tool 50 are detected by a position and orientation detection means (not shown) provided in the end effector or the slave arm 19. The position and the orientation of the end effector detected by the position and orientation detection means may be output to the slave control unit 42 or may be referenced by the slave control unit 42.

An example of the position and orientation detection means may comprise an encoder provided in each joint axis of the slave arm 19. The position and the orientation may be calculated by solving kinematics from a joint displacement amount of the slave arm 19.

As illustrated in FIG. 1, the display unit 20 is mounted on the same base as the detection unit 10 of the master manipulator 2 and installed in front of the surgeon Op. The display unit 20 comprises a display panel 21 that displays the image acquired by the endoscope device 15. A liquid crystal panel or an organic EL panel may be appropriately selected and employed as the display panel 21. Further, the display panel may be a 3D panel that displays an image capable of being viewed stereoscopically. Various known configurations such as a configuration in which images for right and left eyes can be separated by dedicated glasses or a configuration capable of stereoscopic vision by the naked eye may be appropriately selected and employed as the 3D panel that displays the image capable of being viewed stereoscopically.

An operation when the medical manipulator 1 of the present embodiment configured as described above is used will be described.

When the surgeon Op holds the first grip 3 within the visual field Q1 of the detection unit 10, an image including the first grip 3 and the first markers 5 and the second markers 9 provided on the surface of the first grip 3 is acquired by the capturing unit 11 of the detection unit 10. The image recognition unit 12 specifies coordinates of each of the first markers 5 and each of the second markers 9 based on the image.

Information of the specified coordinates is sent from the output unit 13 to the master control unit 41.

The master control unit 41 calculates the position and the orientation of the main body portion 4 of the first grip 3 and a manipulation input with respect to the moving parts 6 based on the received coordinate information. The master control unit 41 performs a predetermined conversion process for corresponding the position and the orientation and the manipulation input with a coordinate system of the slave arm 19 and the treatment tool 50, the endoscope device 15 or the like mounted on the slave arm 19 (hereinafter referred to as simply as "treatment tool or the like") to generate a manipulation signal for the slave manipulator 14. The generated manipulation signal is transmitted to the slave control unit 42 and sent as a driving signal from the slave control unit 42 to the slave manipulator 19. The slave arm 19 and the treatment tool or the like mounted on the slave arm operate based on the driving signal.

When a plurality of slave arms 19 are used, the first grip 3 to be held by the surgeon Op is corresponded to one of the slave arms. Accordingly, only the corresponded slave arm and the treatment tool or the like mounted on the slave arm are operated by a manipulation input through the first grip 3.

Figure 4:
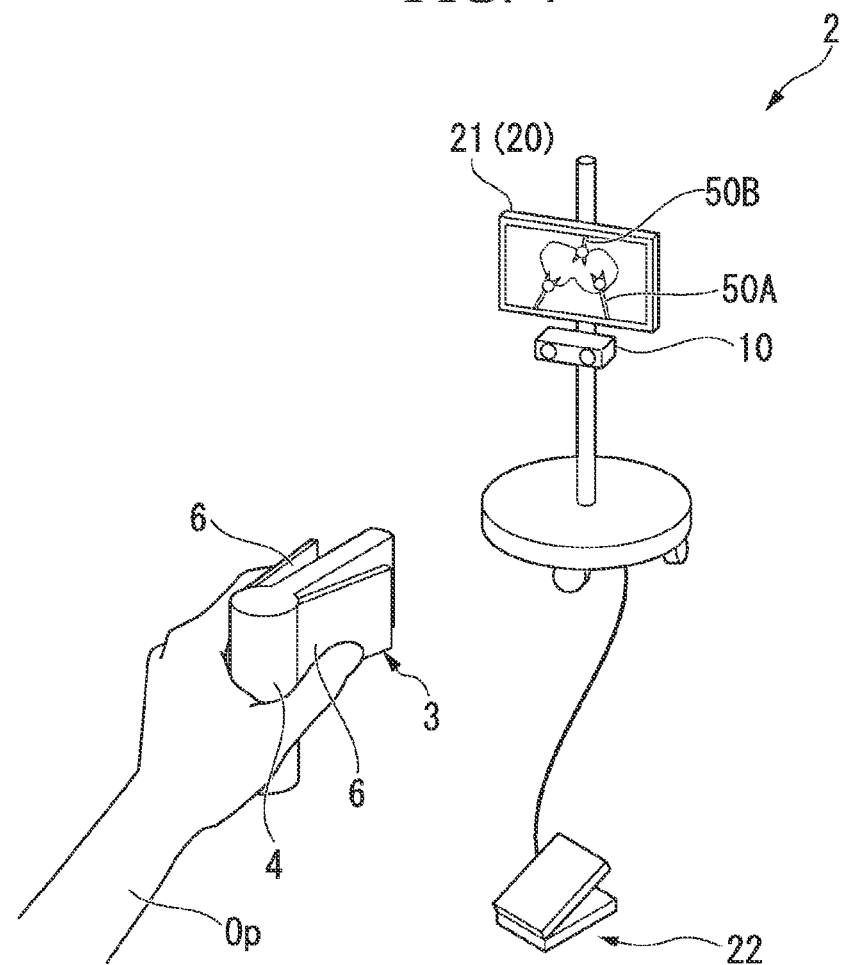
FIG. 4 is a diagram illustrating an operation at the time of use of the medical manipulator according to the first embodiment of the present invention.

When a slave arm different from the currently corresponded slave arm is desired to be manipulated by the master manipulator 2, the surgeon Op steps on a foot switch (an input disconnection unit) 22 illustrated in FIG. 4 to disconnect the master manipulator 2 from the slave manipulator 14 so that the slave manipulator 14 does not operate according to the manipulation input. Then, the slave arm desired to be manipulated is input from an interface (not shown) to the master manipulator 2 and designated. After that, when the foot switch 22 is then stepped on again, the master manipulator 2 is connected with the slave manipulator 14 again and the slave arm desired to be manipulated is corresponded to the input unit to be held by the surgeon.

Figure 5:
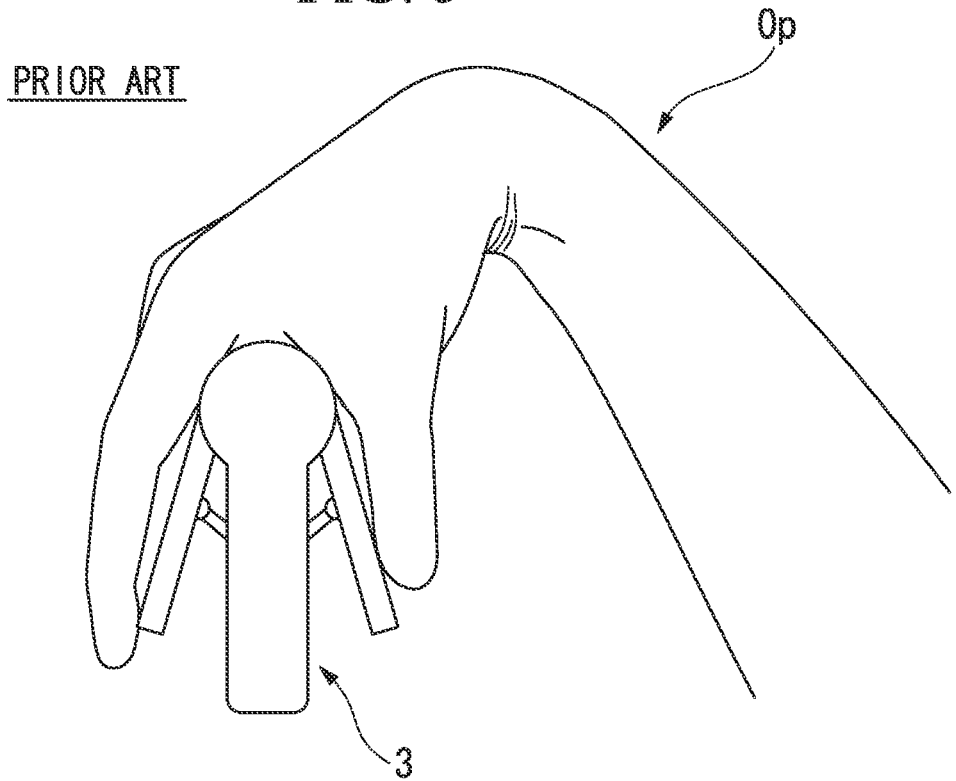
FIG. 5 is a view illustrating an example in which a hand of a surgeon is unnatural at the time of use of a conventional medical manipulator.

Here, for example, when the currently corresponding slave arm and the treatment tool 50A extend from a bottom of the screen of the display panel 21 and the slave arm and the treatment tool 50B desired to be manipulated next extend from a top at an opposite side in the screen as illustrated in the display panel 21 of FIG. 4, directions of the end effectors of the two treatment tools are opposite. For this reason, in a conventional medical manipulator, when the end effector of the treatment tool 50B is tried to be intuitively manipulated using the first grip 3, a hand of the surgeon Op holding the first grip 3 should be in an unnatural orientation, as illustrated in FIG. 5. That is, in the conventional medical manipulator, it may be difficult to manipulate the medical manipulator to cause the direction of the first grip 3 to be the same as that of the end effector.

Figure 6:
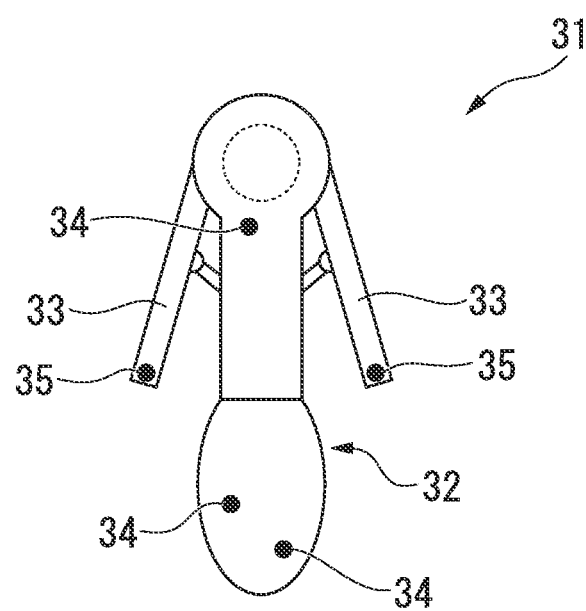
FIG. 6 is a schematic view illustrating a second grip of the medical manipulator according to the first embodiment of the present invention.

In order to prevent this, the surgeon Op switches the held input unit from the first grip 3 to a second grip (a second input unit) 31 illustrated in FIG. 6 and holds the second grip 31. The second grip 31 is an input unit for manipulating the slave arm extending from the top of the screen of the display unit.

FIG. 6 is a schematic view illustrating the second grip 31. A basic structure of the second grip 31 is the same as that of the first grip 3 and comprises a main body portion 32 and a pair of moving parts 33, but greatly differs from the first grip 3 in that the moving parts 33 are rotatably mounted at a distal end side of the main body portion 32. Accordingly, when the surgeon Op holds the second grip 31, the direction of the moving part is opposite to that of the first grip 3.

Further, the second grip 31 comprises first markers 34 and second markers 35, like the first grip, but the markers differ in shape or color from the markers provided in the first grip 3. This enables the detection unit 10 to discriminate and recognize whether the input unit held by the surgeon Op is the first grip 3 or the second grip 31.

Figure 7:
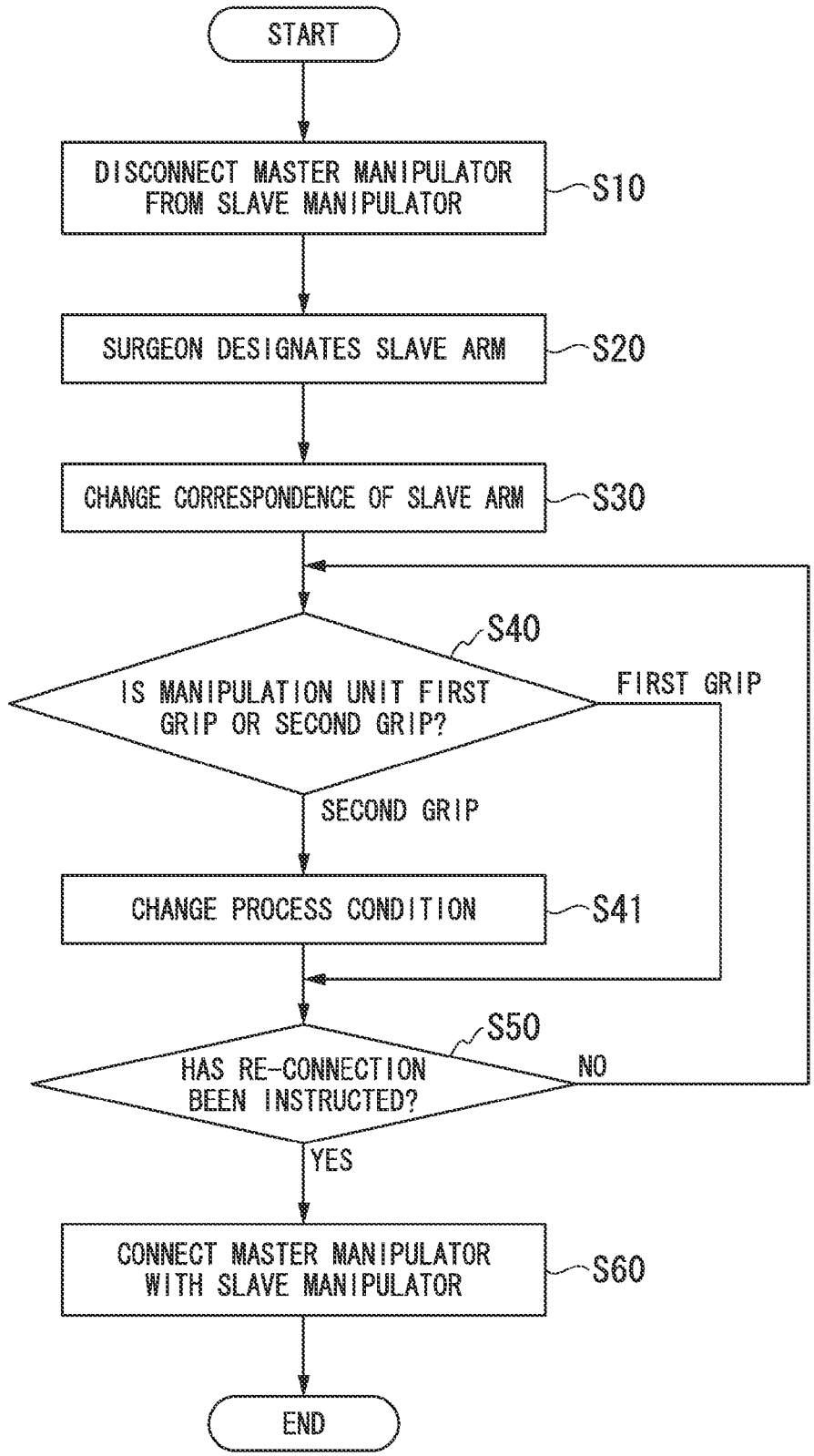
FIG. 7 is a flowchart illustrating a flow of an operation when a slave arm is changed that need a switching of an input unit and held in the medical manipulator according to the first embodiment of the present invention.

An operation when the slave arm is changed according to switching from the first grip 3 to the second grip 31 in the medical manipulator 1 will be described. FIG. 7 is a flowchart illustrating a flow of an operation when the slave arm is changed.

First, in step S10, the surgeon Op steps on the foot switch 22 to disconnect the master manipulator 2 from the slave manipulator 14.

Next, in step S20, the surgeon Op inputs a data of a slave arm to be manipulated after the change to the master manipulator 2 to designate the slave arm.

In step S30, the master control unit 41 changes the slave arm corresponding to the master manipulator 2 into the slave arm designated in step S20.

In step S40, a determination is made as to whether an input unit held by the surgeon Op, that is, currently used is the first grip 3 or the second grip 31. In step S40, when the detection unit 10 recognizes that the surgeon Op holds the same first grip 3 as that before the disconnection, the process proceeds to step S50.

In step S40, when the detection unit 10 recognizes that the surgeon Op holds the second grip 31, which is different from that before the disconnection, the process proceeds to step S41. In step S41, the master control unit 41 reads a coordinate system, a kinematics calculation method or the like set for the second grip 31 from a storage means (not shown) such as a memory in advance, and sets it as a process condition at the time of a subsequent generation of the manipulation signal in the master control unit 41. When step S41 ends, the process proceeds to step S50.

In step S50, the master control unit 41 determines whether the surgeon Op has instructed re-connection of the master manipulator 2 and the slave manipulator 14 through a predetermined manipulation (e.g., by stepping on the foot switch 22 for a certain period of time). When the determination is NO, the process returns to step S40.

When the determination result is YES, the process proceeds to step S60 in which the master control unit 41 connects the master manipulator 2 with the corresponded slave arm 19. Then, the master control unit 41 generates a manipulation signal to be transmitted to the slave control unit 42 based on a manipulation input to the master manipulator 2 and the set process condition using the set process condition.

Figure 8A:
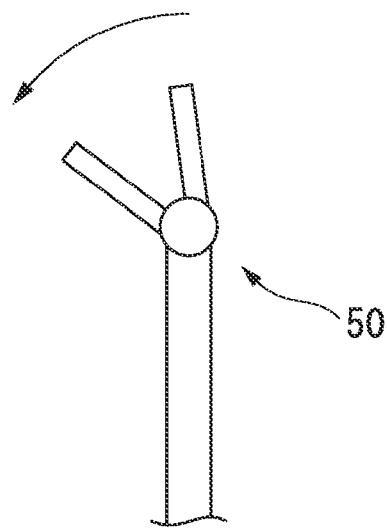
FIG. 8A is a view illustrating a process condition of the first grip.
Figure 8B:
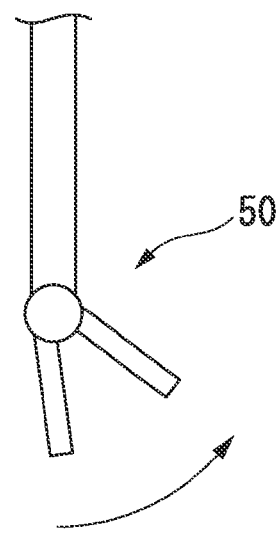
FIG. 8B is a view illustrating a process condition of the second grip.
Figure 8B:
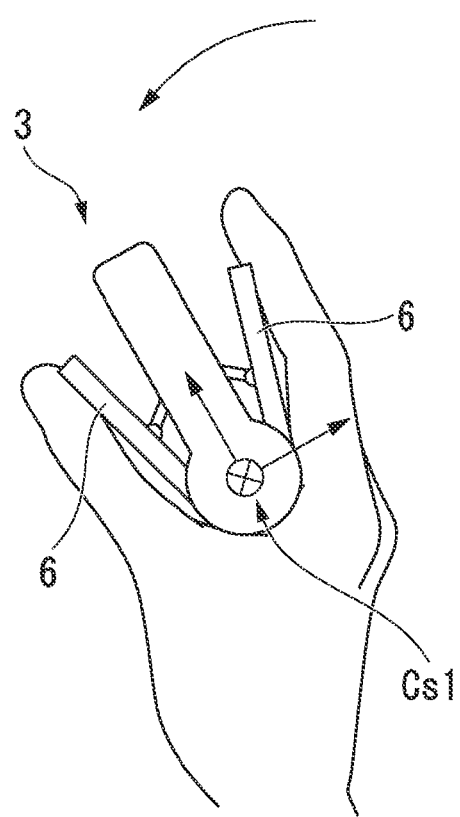
Figure 8B:
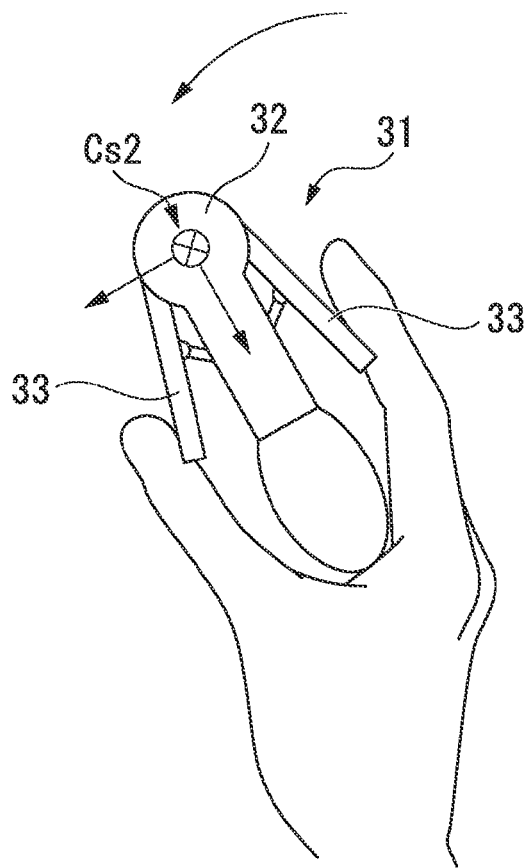

FIGS. 8A and 8B are views illustrating a difference in process condition between the first grip 3 and the second grip 31. With respect to a coordinate system Cs1 of the first grip 3 illustrated in FIG. 8A, a position of an origin of a coordinate system Cs2 in the second grip 31 is set at the distal end side of the main body portion 32 so that the second grip 31 is intuitively manipulated in a hand orientation similar to the orientation when the first grip is manipulated, as illustrated in FIG. 8B. Further, a direction of the coordinate is set so that an origin position of the coordinate system set in the input unit matches an orientation of the distal end of the treatment tool 50, to be felt if the surgeon Op holds and moves the distal end of the treatment tool 50.

In the invention described in Japanese Patent Application, First Publication No. 2001-087281, changing a process for a manipulation input through the grip is not sufficiently considered when the grip is exchanged. Accordingly, there is a problem in that it may be difficult for the surgeon to intuitively manipulate the grip depending on a type of the used grip as a process suitable for a shape or a state of the grip, a shape or a state of a corresponding end effector, or a combination thereof is not performed.

According to the medical manipulator 1 of the present embodiment, if the input unit held by the surgeon Op is changed when the manipulated slave arm is switched, the detection unit 10 recognizes the changed input unit, and a process condition when the master control unit generates a manipulation signal is changed into predetermined content corresponded with the recognized input unit. Accordingly, the surgeon need not change the coordinate system or the kinematics calculation method and can continue to perform the intuitive manipulation only by changing the held input unit even after the slave arm is switched.

Figure 9A:
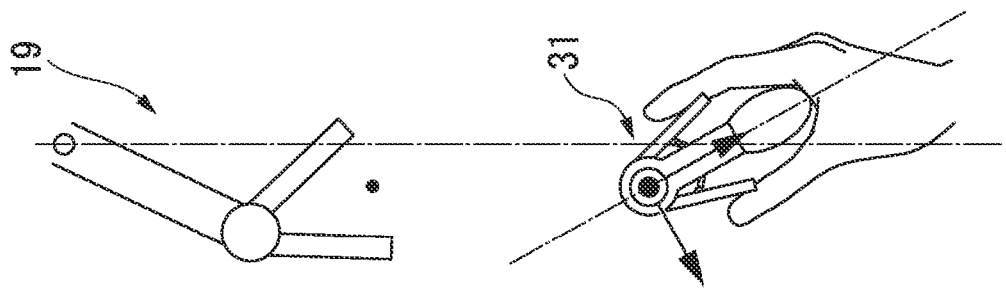
FIGS. 9A to 9C are views illustrating an example of a relationship between a position of a coordinate system in an input unit and an operation of an end effector.
Figure 9B:
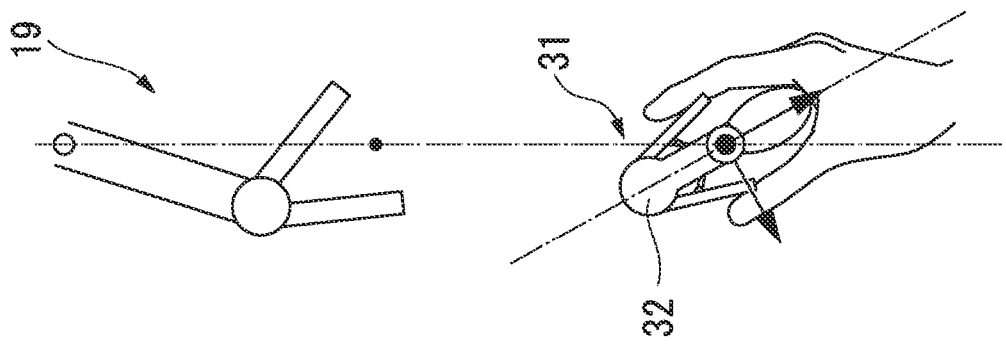
Figure 9C:
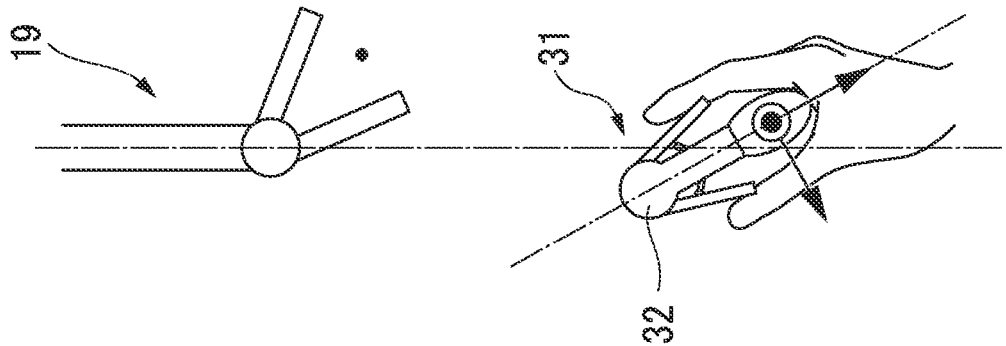

In the present embodiment, the origin of the coordinate system in the second grip 31 may be appropriately set. For example, the origin may be set to an intermediate portion in a longitudinal direction of the main body portion 32 as illustrated in FIG. 9B or may be set to an end portion that is a proximal end side when the main body portion 32 is held, as illustrated in FIG. 9C. In this case, if the coordinate system and the kinematics condition at the slave arm 19 side is assumed to have been fixed, an operation of the slave arm 19 and the end effector is changed due to setting of the origin of the coordinate system in the second grip 31 that is the input unit, as illustrated in FIGS. 9A to 9C, even when a manipulation input with respect to the second grip 31 is the same. How to set the origin of the coordinate system may be determined in light of preference of the surgeon, ease of a manipulation, or the like. Further, the origin may be finely adjusted by an input from the surgeon to an interface after the slave arm is switched.

Further, while the example in which the surgeon designates a slave arm to be manipulated after switching has been described in the present embodiment, this designation may be unnecessary. Hereinafter, such a modified example is illustrated.

Figure 10:
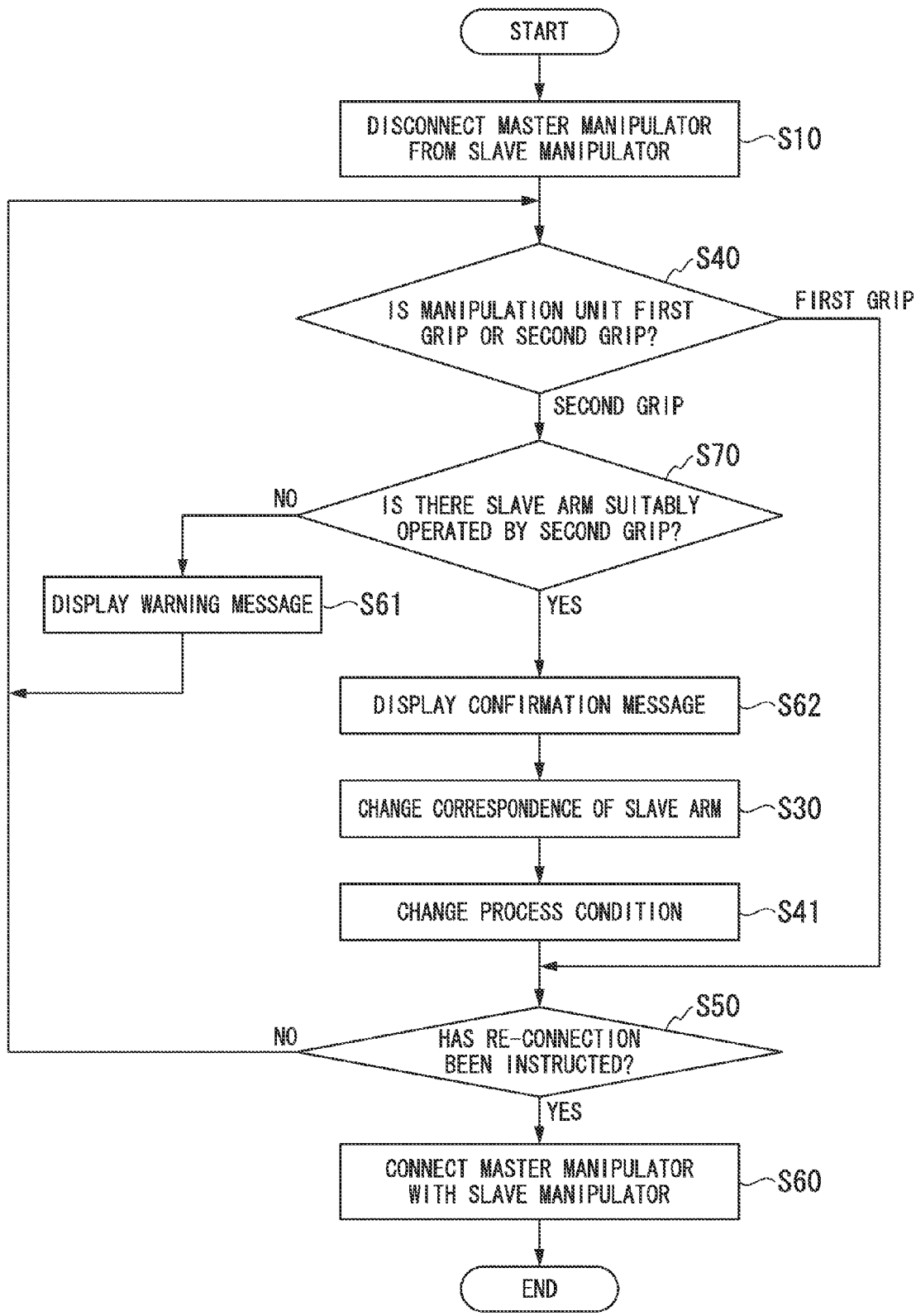
FIG. 10 is a flowchart illustrating a flow of an operation when a slave arm is changed that need a switching of an input unit and held in a modified example of the first embodiment of the present invention.

FIG. 10 is a flowchart illustrating a flow of an operation when the slave arm is changed in a modified example of the present embodiment.

In step S10, for example, when a surgeon changes a corresponding slave arm, as in the example described above, after the master input unit is disconnected from the slave manipulator, the surgeon holds the second grip 31 suitable for a manipulation of the slave arm, particularly, without designating the slave arm.

The process proceeds from step S10 to step S40, not via step S20 and S30, and a type of input unit held by the surgeon Op are discriminated.

In step S40, when the detection unit 10 recognizes that the input unit held by the surgeon Op is changed, that is, the surgeon Op holds the second grip 31, the process proceeds to step S70. In step S70, the master control unit 41 determines whether there is a slave arm suitably manipulated by the second grip 31 based on a positional relationship of another slave arm with respect to a slave arm manipulated before disconnection. When the determination is NO, the process proceeds to step S61 in which the master control unit 41 displays a warning message such as "Since there is no slave arm that can be suitably manipulated by this grip, switch to the first grip and hold it," on the display unit 20. The process then returns to step S40.

When the determination in step S40 is YES, the process proceeds to step S62. In step S62, the master control unit 41 highlight-displays the slave arm or indicates the slave arm using a cursor so that the slave arm can be identified from other slave arms on the display unit 20, displays a confirmation message such as "Is this slave arm manipulated?" and waits for the surgeon Op to perform a confirmation input. When there is a plurality of slave arms, a message urging the surgeon Op to select one slave arm may be displayed on the display unit 20.

If the confirmation input is performed by the surgeon Op, the process proceeds to step S30 in which correspondence of the slave arm is changed. Further, the process proceeds to step S41 in which a process condition is changed. Then, a flow after the process proceeds to step S50 is similar to that in the first embodiment.

Thus, in the medical manipulator of the present embodiment, the master control unit selects a slave arm or its candidate that is suitably manipulated, based on the type of input unit recognized by the detection unit, thereby realizing switching of the slave arm without requiring a designation by the surgeon Op.

Further, in the above modified example, for example, if there was only one slave arm in the determination in step S60, the display of the confirmation message and the confirmation input by the surgeon may be omitted and the master control unit may automatically perform selection of the slave arm and setting of the process condition according to the input unit.

Next, a second embodiment of the present invention will be described. A medical manipulator of the present embodiment and the medical manipulator of the first embodiment differ in a shape of the input unit. In the following description, the same reference numerals are assigned to a configuration overlapping that already described and a description thereof is omitted.

Figure 11A:
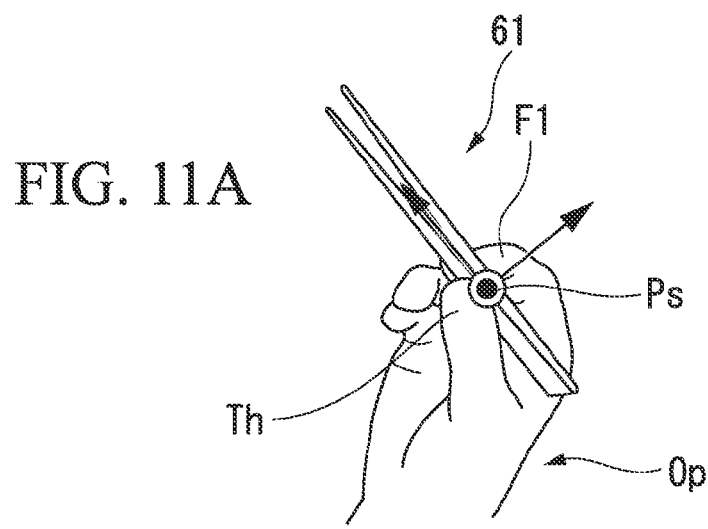
FIGS. 11A to 11C are views illustrating an input unit of a medical manipulator according to a second embodiment of the present invention.
Figure 11B:
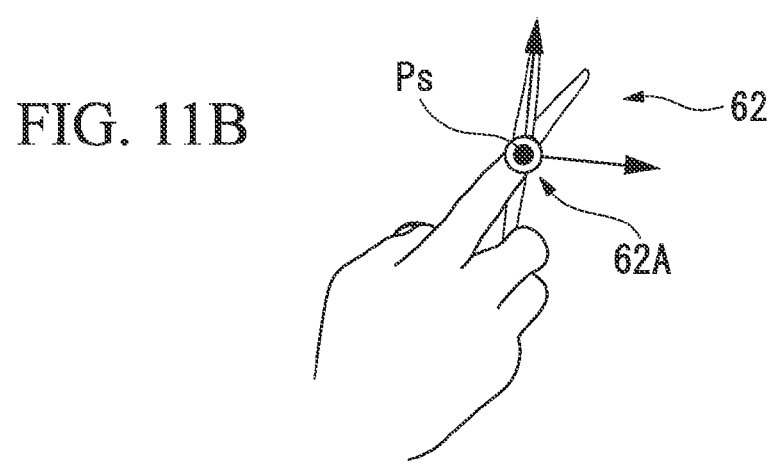
Figure 11C:
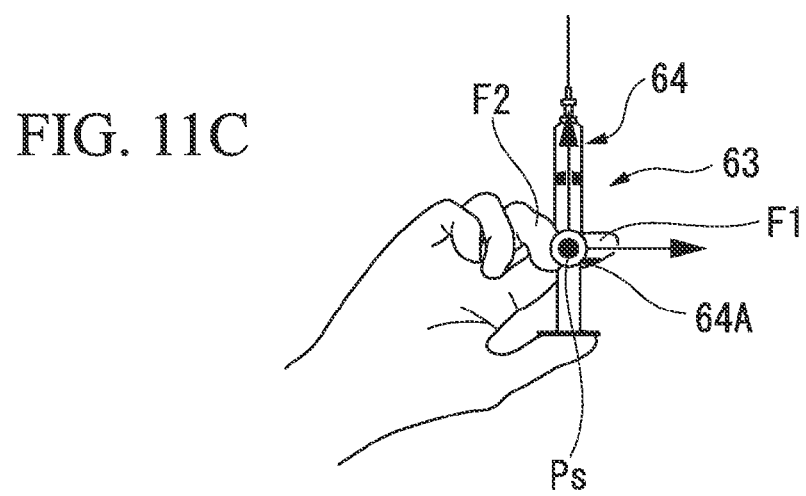

FIGS. 11A to 11C are views illustrating a first grip 61, a second grip 62, and a third grip 63 that are input units in the medical manipulator of the present embodiment, respectively. Each of the grips 61, 62 and 63 in the present embodiment has a shape resembling a tool having the same function to the end effector of the corresponding treatment tool. Specifically, the first grip 61 is of a tweezers type, the second grip 62 is of a scissors type, and the third grip 63 is of a syringe type.

When the end effector of the treatment tool is changed, a reference position for a suitable manipulation at the time of manipulation is also changed. That is, in each end effector, there are a reference position and a coordinate system in which a general surgeon can perform an intuitive manipulation. The coordinate position of the reference position may be a position familiar due to use in usual surgery or a coordinate position that is easily discernible by a person manipulating a specific shape. For example, use of a coordinate system in which the reference position is set to a portion at which a thumb Th and an index finger F1 of the surgeon Op holding the grip contact as illustrated in FIG. 11A when the grip is of a tweezers type, to a rotation axis 62A that is a center of relative rotation of two members each having a blade as illustrated in FIG. 11B when the grip is of a scissors type, or to a proximal end portion 64A of a cylinder 64 to which an index finger F1 and a middle finger F2 of the surgeon Op can be suspended as illustrated in FIG. 11C when the grip is of a syringe type makes it easy to perform the intuitive manipulation.

In the present embodiment, based on this, the coordinate system is set with a portion suitable for the corresponding end effector being a reference position Ps in each of the grips 61, 62 and 63, and the set coordinate system and the set reference position are set as the process conditions in the master control unit according to a type of the grip recognized by the detection unit 10.

According to the medical manipulator of the present embodiment, the surgeon can continue to perform the intuitive manipulation only by exchanging the input unit, as in the first embodiment.

Further, since each of the grips 61, 62 and 63, which are input units, has a shape of a tool having the same function as the corresponding end effector, a more intuitive manipulation can be realized.

As illustrated in the present embodiment, a type of the input unit comprised in the medical manipulator is not limited to two types, and three or more types of input units may be comprised. When three or more types of input units are comprised, a predetermined process condition corresponded to the recognized input unit being set in the master control unit in at least two of the input units is included in the technical scope of the present invention.

Further, in the present embodiment, all the input units may not have the shape of the tool having the same function as the corresponding end effector. Thus, at least one input unit may have such a shape.

Next, a third embodiment of the present invention will be described with reference to FIGS. 12 and 13. A medical manipulator of the present embodiment differs from the medical manipulator of each embodiment described above in that a degree of freedom is changed in the process condition set for each input unit.

Figure 12:
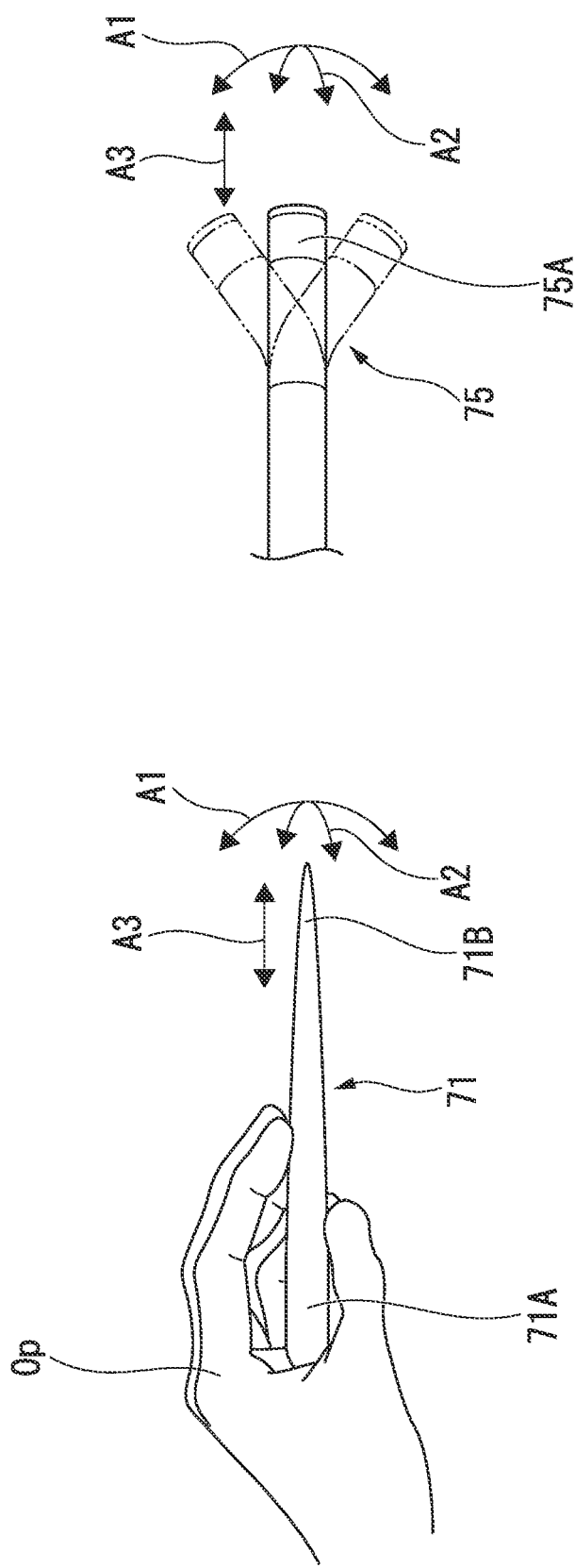
FIG. 12 is a view illustrating a movement of a first grip and a manipulated end effector in a medical manipulator according to a third embodiment of the present invention.

FIG. 12 illustrates a first grip 71 in the medical manipulator of the present embodiment. The first grip 71 has an elongated rod shape. A surgeon Op holds a first end portion 71A of the first grip 71 and performs a manipulation. In the present embodiment, the first grip 71 of the manipulation unit is capable of an input with six degrees of freedom of position and orientation, but a slave has only three degrees of freedom (yaw, pitch, and linear motion). In this case, for an input value of the six degrees of freedom of the manipulation unit, there is a plurality of combinations of movements of a slave with three degrees of freedom.

The first grip 71 having a rod shape has a structure in which it is easy for movements of three degrees of freedom, i.e., fluctuation (an arrow A1 in FIG. 12) within a first surface passing through an axis line of the first grip 71 around the first end portion 71A that is held, fluctuation (an arrow A2 in FIG. 12) within a second surface, perpendicular to the first surface, passing through the first grip 71, and advance or retreat (an arrow A3 in FIG. 12) in a direction parallel to the axis line of the first grip 71 among the movements of six degrees of freedom to be intuitively discernible by the surgeon. In the medical manipulator of the present embodiment, when the detection unit 10 recognizes the first grip 71, a process condition is set so that the master control unit 41 generates a manipulation signal using only an input value of the three degrees of freedom. Then, manipulation is performed with the second end portion 71B of the first grip 71 being the reference position, so that the distal end 75A of the end effector 75 is correspondingly moved.

Figure 13:
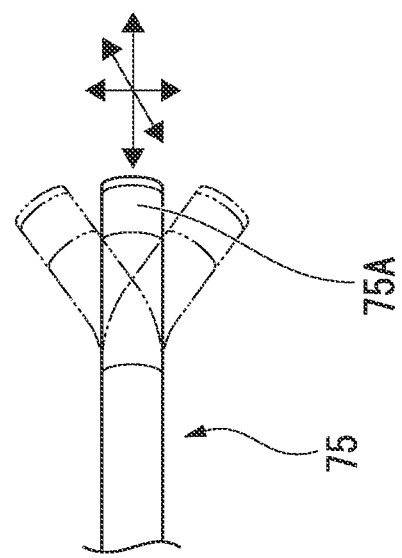
FIG. 13 is a view illustrating a movement of a second grip and a manipulated end effector in the medical manipulator according to the third embodiment of the present invention.
Figure 13:
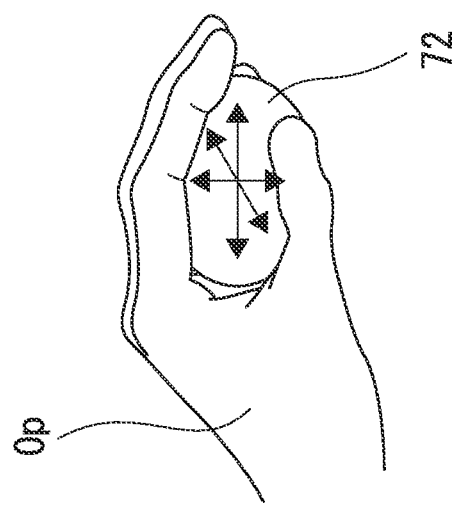

FIG. 13 illustrates a second grip 72 in the medical manipulator of the present embodiment. The second grip 72 is formed in a substantially spherical shape, and a surgeon Op holds a whole of the second entire grip 72 to be wrapped by his or her hand. For an input value of six degrees of freedom of the manipulation unit, there is a plurality of combinations of movements of a slave with three degrees of freedom, similar to the first grip 71 described above.

Here, in the grip held so as to be wrapped by hand, for example, it is easy for a motion of the entire grip to a desired position to be intuitively discernible by the surgeon, like a mouse for a computer. When the detection unit 10 recognizes the second grip 72, the process condition is set so that the master control unit 41 generates a manipulation signal using only a predetermined position of the second grip 72, for example, input values of movement amounts in three axes that are perpendicular at a center of gravity. Then, manipulation is performed with a predetermined position at which the three axes are orthogonally set as the reference position, so that the position of the distal end 75A of the end effector 75 is moved corresponding to the reference position.

The medical manipulator of the present embodiment enables the surgeon to continue to perform the intuitive manipulation only by exchanging the input unit, as in each embodiment described above.

Further, since the process condition is set so that, for example, a degree of freedom (a master-slave conversion calculation equation) used to generate the manipulation signal for the slave arm and the treatment tool among command values of six degrees of freedom input from the manipulation unit is selected as a predetermined degree of freedom corresponded in advance, according to the input unit held by the surgeon, the intuitive manipulation can be suitably performed.

While each embodiment of the present invention has been described above, the technical scope of the present invention is not limited to the embodiment described above, and a combination of components may be changed, various changes may be made to each component, or any of the components may be deleted without departing from the scope and spirit of the present invention.

First, in the present invention, content of the process condition set in the manipulation signal generation unit based on a type of an input unit recognized by the detection unit is not limited to the above-described content.

For example, various control parameters such as a motion scale ratio, a type or strength of a filter used at the time of signal generation, an operation speed, and a current limit value of the slave manipulator (an output limit value of the manipulation signal) may be comprised in the process condition. Hereinafter, some concrete examples are suggested.

When the end effector is a needle holder for which fine manipulation is frequently performed, a motion scale ratio set when a corresponding input unit is recognized is set to a great value and a reduced manipulation is delivered to the slave. When the end effector is a tissue retractor for which dynamic manipulation is frequently performed, a motion scale ratio set when a corresponding input unit is recognized is set to a small value and an expanded manipulation is delivered to the slave. Accordingly, an intuitive and easy manipulation can be realized.

When the end effector is a needle holder, a process condition is set so that a predetermined filter is strongly applied to a manipulation input when a corresponding input unit is recognized, thereby suppressing jiggling of the end effector and realizing a suitable manipulation.

When the end effector is a pair of scissors, a motion speed set when a corresponding input unit is recognized is set to a high value, making smooth incision possible.

When the end effector is a grip forceps for gripping an organ, a current limit value of a motor or the like for driving the end effector is set to a high value when a corresponding input unit is recognized. Accordingly, great force is generated by the end effector, thereby suitably gripping a tissue.

Further, while the example in which the first input unit and the second input unit are separate entities has been described in each embodiment described above, the first input unit and the second input unit may be realized as a single grip.

Figure 14A:
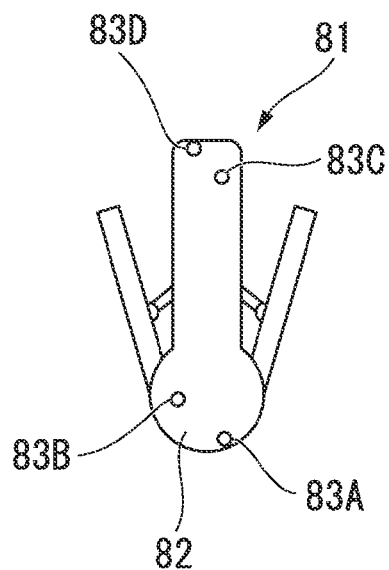
FIG. 14A is a view illustrating a grip in a modified example of the present invention.

FIG. 14A is a view illustrating a grip 81 in such a modified example. Four markers 83A to 83D are provided as first markers in a main body portion 82. Second markers are not shown.

Figure 14B:
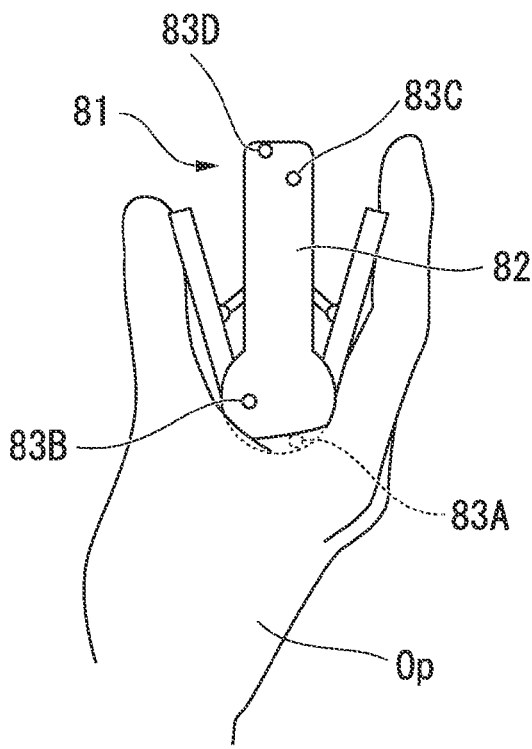
FIG. 14B is a view illustrating a holding state in which the grip is recognized as a first grip.

When a surgeon Op holds the main body portion 82 of the grip 81 as illustrated in FIG. 14B, the marker 83A among the four first markers is covered by a hand of the surgeon Op and is not detected by the detection unit 10. As a result, only the three markers 83B to 83D are recognized as the first markers, and the detection unit 10 recognizes that a first input unit is held.

Figure 14C:
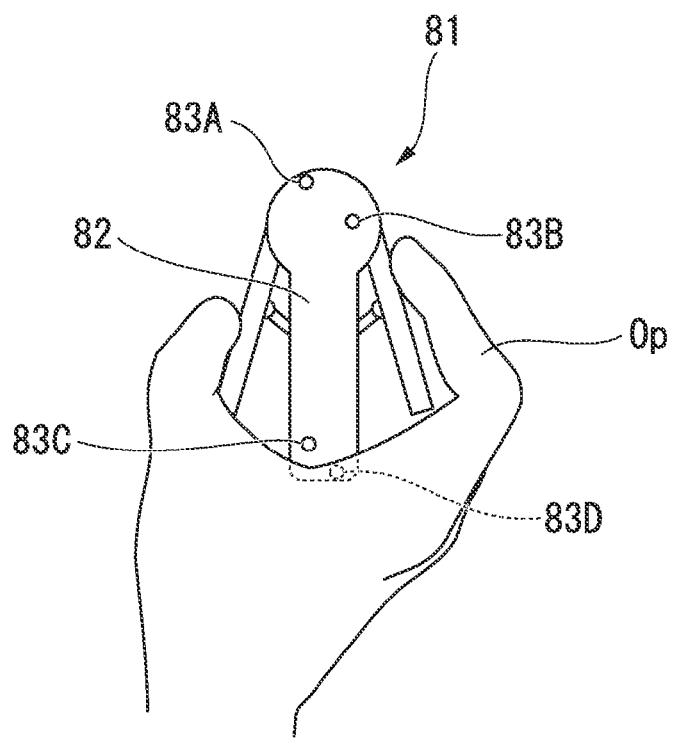
FIG. 14C is a view illustrating a holding state in which the grip is recognized as a second grip.

When the surgeon Op holds the main body portion as illustrated in FIG. 14C, the marker 83D among the four first markers is covered by the hand of the surgeon Op and is not detected by the detection unit 10. As a result, only the three markers 83A to 83C are recognized as the first marker, and the detection unit 10 recognizes that a second input unit is held.

In this modified example, even when only one grip 81 is comprised, the detection unit 10 is capable of being created two states, such as a state in which the grip is recognized as the first input unit and a state in which the grip is recognized as the second input unit, depending on how the grip 81 is held. Accordingly, it is possible to achieve the effect of the present invention.

Further, an input mechanism common to the first input unit and the second input unit may be comprised and the process condition may be set so that a function exhibited by an input with respect to the input mechanism is changed by a type of the input unit recognized by the detection unit.

For example, in an example in which all of a plurality of input units comprise a button, the following function switching can be realized.

When the end effector is the needle holder, a state in which a jaw is closed is maintained by a button manipulation input so that a curved needle is capable of being persistently held. When the end effector is a high-frequency treatment tool, power on/off of the treatment unit is capable being realized by a button manipulation input. When the end effector is a suturing device such as a stapler or a clip, suturing may be performed by a button manipulation input. When the end effector is an endoscope, zooming may be performed or a still image may be acquired by a button manipulation input.

Since the above is only an example, it is understood that various other functions may be assigned to various end effectors.

The common input mechanism is not limited to the button, and the common input mechanism may be an analog knob such as a slide type knob or a rotation type knob or may be the moving part described above. For example, an input unit for a treatment tool whose end effector is not a forceps may comprise a moving part 6 and the process condition may be set so that a function other than opening or closing of the forceps is exhibited by an input with respect to the moving part 6.

Further, while the example in which the input unit is not physically connected with the manipulation unit has been described in each embodiment described above, the manipulation unit is not limited to such a configuration. Accordingly, physically, the input unit may be detachably mounted on and exchangeable with respect to the manipulation unit. In this case, the input unit to be held by the surgeon may not necessarily be discriminated through image processing. For example, the input unit has an identification unit such as a pin, which has information such as a type and is inserted into the manipulation unit when the input unit is detachably mounted is comprised, and when the input unit is mounted, the detection unit acquires the information such as the type of the input unit from the identification unit.

Further, the medical manipulator of the present invention is not limited to the operating unit being remotely manipulated. Accordingly, even in a medical manipulator in which the manipulation unit and the operating unit are physically connected, the present invention can be applied with no problems and the above-described effect can be achieved.

Further, in the medical manipulator of the present invention, a plurality of input units may be simultaneously manipulated and a plurality of operating units corresponding to the respective input units may be simultaneously operated.

In addition, the present invention is not limited to the above description and is limited only by appended claims.

What is claimed is:
1. A medical manipulator comprising:
    a plurality of input units selectively used by an operator, wherein one of the plurality of input units is used at a time by the operator;
    an operating unit configured to have a plurality of slave arms, each of the plurality of slave arms corresponding to one of the plurality of input units;

an imaging sensor configured to acquire image data of one of the plurality of input units which is currently used by the operator; and a processor comprising hardware, the processor being configured to recognize the one of the plurality of input units which is currently used by the operator as a currently used input unit based on the image data acquired by the imaging sensor; and the processor being configured to access a plurality of process conditions, each of the plurality of process conditions corresponding to one of the plurality of input units;

the processor being further configured to generate a manipulation signal by processing an input with respect to the currently used input unit based on one of the process conditions which corresponds to the currently used input unit, wherein the process conditions are different from each other, and one of the plurality of slave arms which corresponds to the currently used input unit is selectively operated by the manipulation signal.

2. The medical manipulator according to claim 1, wherein one of the plurality of process conditions which corresponds to the currently used input unit includes a setting aspect of a coordinate system in the currently used input unit.

3. The medical manipulator according to claim 1, wherein one of the plurality of process conditions which corresponds to the currently used input unit includes an origin position of a coordinate system in the currently used input unit.

4. The medical manipulator according to claim 1, wherein one of the plurality of process conditions which corresponds to the currently used input unit includes information for selecting degrees of freedom used for generation of the manipulation signal among degrees of freedom included in the input.

5. The medical manipulator according to claim 1, wherein:
at least one of the plurality of slave arms has an end effector exhibiting a predetermined function, and
at least one of the plurality of input units has the same shape as a tool exhibiting the function.

6. The medical manipulator according to claim 5, wherein one of the plurality of process conditions which corresponds to the currently used input unit includes a scale ratio of an input to the currently used input unit and the manipulation signal.

7. The medical manipulator according to claim 5, wherein one of the plurality of process conditions which corresponds to the currently used input unit includes information for a filter used at the time of generation of the manipulation signal.

8. The medical manipulator according to claim 5, wherein one of the plurality of process conditions which corresponds to the currently used input unit includes an output limit value of the manipulation signal.

9. The medical manipulator according to claim 1, wherein:
when two of the plurality of input units are defined as a first input unit and a second input unit, the first input unit and the second input unit include a common input mechanism, and
two of the plurality of process conditions which correspond to the first input unit and the second input unit include a type of a function exhibited in the operating unit by an input to the common input mechanism.

10. A method of controlling a medical manipulator including a plurality of input units selectively used by an operator and a plurality of slave arms, each of the plurality of slave units corresponding to one of the plurality of input units, of the input units is used at a time by the operator, each of a plurality of process conditions corresponding to one of the plurality of input units being prepared in advance so that the process conditions are different from each other, the method comprising:
capturing image data of one of the plurality of input units which is currently used by the operator;
detecting the one of the plurality of input units which is currently used by the operator as a currently used input unit based on the captured image data;
generating a manipulation signal by processing an input with respect to the currently used input unit based on one of the plurality of process conditions which corresponds to the currently used input unit; and
operating one of the slave arms which corresponds to the currently used input unit by using the manipulation signal.

11. A medical manipulator comprising:
a manipulation unit configured to have a first input unit and a second input unit that are exchangeable and manipulated by an operator;
an image sensor configured to capture an image of at least one of the first input unit and the second input unit;
a processor comprising hardware, the processor being configured to:
discriminate between the first input unit and the second input unit, recognize the first input unit and the second input unit, and acquire coordinates of the first input unit and the second input unit in a visual field of the capturing unit, from an image captured by the image sensor;
output the coordinates as coordinate information; and
perform a process based on a predetermined process condition using the coordinate information to generate a manipulation signal; and
an operating unit mounted on a treatment tool and configured to be operated by the manipulation signal,
wherein the process condition corresponding to the first input unit and the process condition corresponding to the second input unit differ from each other, and
the processor is further configured to generate the manipulation signal based on the process condition corresponding to the recognized one of the first and second input units.

12. The medical manipulator according to claim 11, wherein
the first input unit has a first marker having a visual feature specific to the first input unit,
the second input unit has a second marker specific to the second input unit, the second marker being capable of being visually discriminated from the first marker, and
the processor discriminates between the first marker and the second marker, recognizes the first marker and the second marker, and acquires coordinates of the first marker and the second marker in the visual field of the image sensor, from the image captured by the image sensor.

13. The medical manipulator according to claim 11, wherein the process condition includes a setting aspect of a coordinate system in the input unit.

14. The medical manipulator according to claim 11, wherein the process condition includes an origin position of a coordinate system in the input unit.

15. The medical manipulator according to claim 11, wherein the process condition includes information for selecting degrees of freedom used for generation of the manipulation signal among degrees of freedom included in an input.

16. The medical manipulator according to claim 11, wherein
   the operating unit includes an end effector exhibiting a predetermined function, and
   at least one of the first input unit and the second input unit has a shape similar to a shape of a known medical device capable of exhibiting the predetermined function.

17. The medical manipulator according to claim 16, wherein the process condition includes a scale ratio of an input to the input unit and the manipulation signal.

18. The medical manipulator according to claim 15, wherein the process condition includes information for a filter used for suppressing generation of the manipulation signal based on a predetermined input of inputs that have been input to the input unit when the manipulation signal is generated.

19. The medical manipulator according to claim 16, wherein the process condition includes an output limit value of the manipulation signal.

20. The medical manipulator according to claim 11, wherein
   the first input unit and the second input unit include an input mechanism configured to be operated with a common input operation by a manipulating person, and
   the process condition includes a type of a function exhibited in the operating unit by an input to the input mechanism.

* * * * *